US005723718A

United States Patent [19]
Berens

[11] Patent Number: 5,723,718
[45] Date of Patent: Mar. 3, 1998

[54] INDUCTION OF IMMUNE TOLERANCE TO TUMOR CELLS

[75] Inventor: Michael E. Berens, Gilbert, Ariz.

[73] Assignee: St. Joseph's Hospital and Medical Center, Phoenix, Ariz.

[21] Appl. No.: 359,760

[22] Filed: Dec. 20, 1994

[51] Int. Cl.⁶ .............................. C12N 5/00; C12N 15/00
[52] U.S. Cl. ......................... 800/2; 424/93.7; 424/93.1; 800/DIG. 5; 435/172.3
[58] Field of Search ................................ 435/1.1, 172.1, 435/240.2, 172.3, 93.7; 424/93.1, 93.21, 85; 800/2, DIG. 1–4

[56] References Cited

U.S. PATENT DOCUMENTS 4,276,282   6/1981   Sugimoto et al. .................... 424/85

OTHER PUBLICATIONS

Tizard, Veterinary Immunology. ISBN 0–7216–8868–3, published by W. B. Saunders Company, p. 157, 1977.
Shifrine, M., et al., "Leukemia Allotransplants in Canine Fetuses: Influence of Host Age and Immune Responsiveness", *Proceedings of the Society of Experimental Biology and Medicine*, 151:307–309 (1976).
Tizard, I., "Immunity in the Fetus and Newborn", *Veterinary Immunology: An Introduction*, 3rd vol., CWB Saunders Co., Philadelphia, (1987).
Bates, Robert W. et al. Induction of Permanent Diabetes in Rats by Pituitary Hormones from a Transplantable Mammotropic Tumor, Concomitant Changes in Organ Weights and the Effect of Adrenalectomy, Apr. 1966, pp. 826–836.

*Primary Examiner*—Jasemine C. Chambers
*Assistant Examiner*—Deborah J. R. Clark
*Attorney, Agent, or Firm*—Townsend and Townsend and Crew LLP

[57] ABSTRACT

The present invention provides methods of producing a canine animal model of cancer. The method comprising introducing a heterologous tumor cell into an pre-mature, preimmunocompetent canine animal under conditions that induce immune tolerance to the tumor cell. The tumor cell is then allowed to proliferate in the canine animal, thereby forming a tumor.

21 Claims, 1 Drawing Sheet

INDUCTION OF IMMUNE TOLERANCE TO TUMOR CELLS

BACKGROUND OF THE INVENTION

Studies of cancer biology and the development of new treatments for cancer largely depend on in vitro methods. These laboratory techniques have helped clarify the biochemistry, genetics, and growth properties of certain types of tumors. Tissue culture studies also offer a practical method of screening natural (extracted) and synthetic sources for potential antitumor agents. In vitro screening of antitumor agents may identify cytotoxic compounds but fails to account for modifications imposed by pharmacological, physiological, toxicological, immunological and other biological influences that occur when treating a whole animal and which can profoundly impact treatment of a patient. Advancing new therapies for clinical use is, therefore, a complex, tedious and slow process.

Very large numbers of patients are required to generate reliable data for the development and testing of new therapies for two reasons. First, there is considerable individual variation in patient populations. Second, patients with the same disease become symptomatic in a wide range of stages in the course of the disease. Consequently, the slow pace of improving cancer treatments that reflect this fact of medicine is exacerbated for cancers that occur less frequently (e.g., brain tumors).

Animal models of cancer are desirable for several reasons. First, they potentially overcome the variation present in human populations. Second, they accelerate the pace of cancer studies in live animals. Finally, they avoid exposing humans to risks from highly novel therapies. This latter limitation especially applies to therapies being developed with modern molecular biology strategies and newer immunological approaches (e.g., gene repair technology, monoclonal antibodies, immune therapy, biological response modifiers, new cytotoxic agents). To the degree that an animal cancer is like human cancer, the animal studies model the disease.

Because the incidence of cancer in animals is low, transplantable tumors from arcinogen-induced cancers have been developed in inbred strains of rodents (mice and rats). Inbred animals may serve effectively as hosts for transplanted tumors from the same strain. Genetic inbreeding, however, also may select for other, unidentifiable genetic and biochemical changes that could compromise the utility of the model. Carcinogen- or viral-induced cancers are antigenically and genetically unlike cancers that arise spontaneously. Furthermore, as the pace of research into the human genome accelerates, the more human-like a model is, the more likely it will assist in studies of the molecular genetics of cancer. For these reasons, rodent tumors have limited utility in predicting response of their human tumor counterparts.

Methods exist for propagating human tumor cells in experimental animals (usually rodents). The critical manipulation is altering the host's immune system to avoid immune rejection of the transplanted tumor. Several methods allow a xenogeneic (usually human) tumor to be grown in an animal. For instance, the thymus gland can be removed surgically during an animal's development to preclude the establishment of a normal immune system. In addition, adult animals have been treated with drugs or radiation (e.g., cyclosporin or x-rays) to suppress the immune system. In yet another approach, animals have been bred selectively to maintain a genetic defect that manifests as an absent or deficient immune system (e.g., athymic or SCID mice). Each of these methods allows human tumors to grow in the animal. Because of the immune manipulation used, however, therapies that rely initially or partially on an immune response cannot be tested in these animals.

Very recently, genetic engineering methods have been used to introduce cancer-causing genes (oncogenous) into the fertilized eggs of rodents. These genes are genetically engineered to be regulated by control processes specific to certain tissues that differentiate during development. When the tissue-specific regulation processes commence, the "transgenic" animal activates the oncogene and a tumor may develop. Although each of these models induces a solid tumor to grow in an animal, each is limited by a lack of concurrence with spontaneously arising tumors in normal animals. These limitations hinder the development and testing of new cancer therapies.

Thus, there exists a need for a reproducible model using nonhuman animals with normal immune systems to serve as (more relevant) superior hosts for transplants of spontaneously arising tumors, and for various other applications, including screening for immunomodulatory agents, antineoplastic agents, and therapeutic agents that may prevent or inhibit cancer. The present invention addresses these and other needs.

SUMMARY OF THE INVENTION

The present invention provides methods of producing canine animal models of cancer. The methods introduce heterologous tumor cells into a pre-mature, pre-immunocompetent canine under conditions that induce natural immune tolerance to the tumor. The tumor cells then proliferate in the canine, thereby forming a tumor. If necessary, once the tumor is established, it can be transplanted from its initial implanted location to other organs or sites representative of the natural occurrence of the tumor.

The immature animal must be a fetus. In preferred embodiments, the animal is a fetus, typically between about 35 and 40 days old. In most preferred embodiments, the fetus is 36 to 38 days old.

A variety of heterologous tumor cells can be used to tolerize the animal. In preferred embodiments, the tumor cell is xenogeneic. In most preferred embodiments, the tumor cell is from a human tumor. As canines are especially useful for the study of brain cancers, the tumor cell is typically from a brain tumor.

The tumor cell can be introduced into the immature animal in a number of sites; preferably, it is introduced subcutaneously. To optimally model spontaneous tumors, the tumor should grow in the correct organ or anatomical region. The methods may comprise the step of transplanting the initial subcutaneous tumor to a desired organ in the animal.

The mechanism for rejecting heterologous cells is believed to involve recognition of surface molecules on the transplanted cells. The best understood surface molecules that lead to tissue rejection are products of the Major Histocompatibility Complex (MHC). In general, all the cells in an animals body, whether normal or tumor cells, express the same MHC proteins. Consequently, the methods of the invention may also comprise introducing nontumor (normal) cells derived from the same patient (human or animal) from which the tumor cells were derived, or introducing appropriate antigens associated with tumor into an immature canine under conditions that induce immune tolerance to the allogeneic tumor cells. Subsequently, a tumor cell expressing the antigen is introduced into the canine animal.

Definitions

As used here, the term "tumor" refers to a solid neoplastic growth that may be either malignant or benign. Malignant tumors are those that invade surrounding tissues and are usually capable of producing metastases. Tumors may be associated with carcinomas, that is, with malignant neoplasms derived from epithelial tissues such as lung, intestine (including colon), prostate, breast or cervical tissue. Alternatively, tumors may arise as neoplasms of the connective tissues, that is, sarcomas. Cancers associated with tumors are distinguished from neoplastic proliferation of abnormal leukocytes found in hematopoietic tissues (e.g., leukemias), which do not result in growth of a solid mass of tissue.

The term "heterologous" refers to tissue or cells derived from a source different from the host animal. Heterologous cells may be allogeneic, (i.e., derived from a different individual of the same species, but with a different genotype). Heterologous cells also may be xenogeneic (i.e., derived from an individual of a different species).

A "premature, pre-immunocompetent canine animal" as used herein refers to an animal whose immune system has not developed to the point where it has lymphocytes capable of discriminating self from nonself. Such an animal is usually at the neonatal (in rodents) or fetal stage of development (in higher mammals). Neonatal refers to the period of life immediately after birth and continuing until about the first 48 hours of life. In canines, immunocompetence develops before birth. For fetal canines, preferred immunoincompetence is before about the 40th day of gestation. Gestation is measured from the day of conception. Gestation can vary among species, among breeds, and even among individuals. For instance, in canines the period may range between 58 and 65 days.

The term "specifically immunotolerant" refers to the condition in which an animal manifests an otherwise normal immune system, but which recognizes a particular heterologous cell or antigen(s) as self. In particular, the term refers to the condition that develops when a foreign protein antigen is introduced into a premature, pre-immunocompetent animal in such a way that the animal develops immune tolerance to the antigen, as if the antigen were a self protein. For example, human brain tumor cells introduced into a fetal canine at the appropriate stage of gestation are recognized as self by the animal's immune system. The animal is immunotolerant of the foreign antigen but has developed an otherwise fully functional, normal immune system. Thus, the animal is specifically immunotolerant of the foreign antigen.

DESCRIPTION OF THE PREFERRED EMBODIMENT

Figure 1:
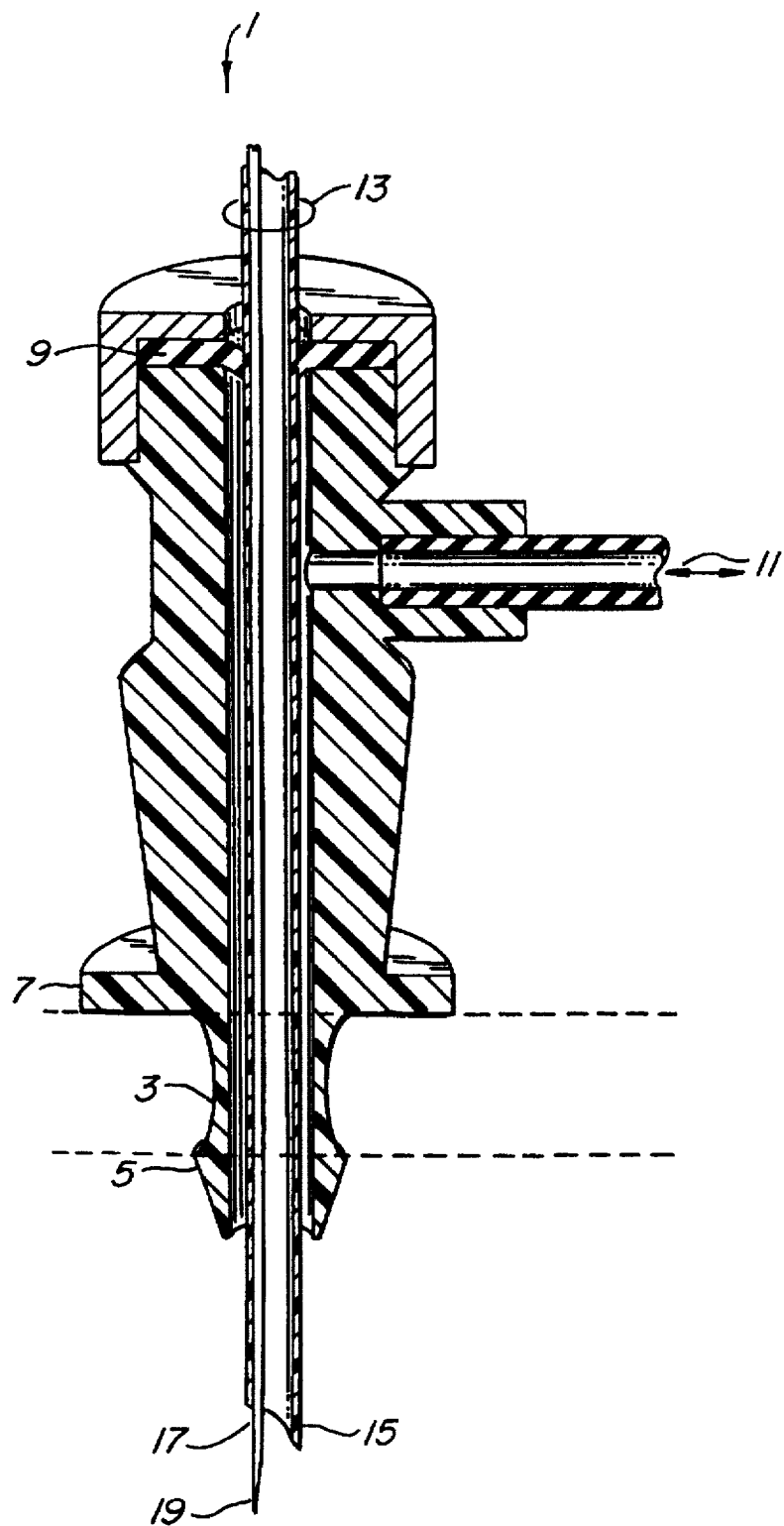
FIG. 1 illustrates an introducer useful in practicing the methods of the invention.

The present invention provides a large animal model of cancer that expedites study of cancer. In particular, the model is useful in the development of new compounds for the treatment and diagnosis of cancer. The model maintains a normal, intact immune system, and the animal demonstrates clinical, genetic and immunological features of the disease that are representative of similar properties in spontaneous human tumors.

A unique aspect of the developed technique is the acquisition of natural immune tolerance, specifically toward the cancer cells from which the tumors arise. The animals, preferably canines, have a normal immune system in all respects with the exception that they do not naturally reject the transplanted tumor cells. Manipulation of the animal's tolerance ensures that the host is essentially a "normal" animal and therefore amenable to a variety of experimental studies, including therapies intended to activate the immune system. This approach yields a novel development for modeling cancer in large animals. In preferred embodiments, canines are used as the animal model. Canines are particularly useful in the invention because the size of the model affords the opportunity to include surgical removal of the tumor as one arm of the treatment regimen when evaluating new therapies.

The mammalian immune system usually prohibits the survival of implanted heterologous cells (xenogeneic or allogeneic), whether these are normal or cancer cells. The methods of the invention induce normal immune tolerance to foreign (tumor cell) antigens in animals, such as canines. These canines can then serve as hosts for the growth of tumors. The genetic and biological utility of the model is enhanced by using tumor cell lines that are derived from spontaneously arising cancers.

Of all domestic animals for which cancer epidemiological data exist, canines show an incidence and histopathology of brain tumors almost identical to humans. Thus, the present invention is particularly useful in developing treatments for brain cancer (e.g., glioma) in canines.

Any number of canine breeds commonly used as models of disease can be used in the present invention. Suitable breeds include beagles.

The methods of the invention are performed by introducing cancer cells or other antigens into a fetal canine animal under conditions that induce immune tolerance to the cells. During fetal development of an animal, cells destined to become the immune system undergo a process referred to as "competency." Immature immune cells circulate throughout the animal or reside in the thymus where they assess specific "self" proteins, which are present on cells in the developing animal. Immature lymphocytes that react with these "self" proteins are eliminated by a process of clonal deletion or are rendered unresponsive (anergic). The consequence of clonal deletion or induction of anergy is that the cells that survive to form the mature immune system are unable to mount an immune response against the host. For a discussion of immunological tolerance, see Schwartz, in *Fundamental Immunology*, 3rd. Ed. W. E. Paul, ed., Chapter 18: Raven Press, New York 1993.

Fetal canines used in the invention are pre-immunocompetent, such that an introduced antigen will be recognized as "self" after the immune system of the animal develops fully. Typically for canines, such immunocompetency begins to develop after the 40th day of gestation. In preferred embodiments, a fetal animal is exposed to the antigen expressed on the tumor cells. Preferably, the cells are introduced to fetal canines during the interval (36th to 38th day of gestation for beagles), before immunocompetence occurs. The correct timing of the introduction ensures clonal deletion or anergy of the immune cells that would react against the foreign tumor cells.

The methods used to introduce the cancer cells or antigen into the immature canine are not, unto themselves, critical to the present invention. However, surgical access to fetal canines at this early stage of gestation is an undeveloped discipline. Implantation techniques for the 36th to 40th day gestational age of canines have been invented as a component of this project. A unique endoscopic introducer has been designed and made. A 37-mm diameter endoscope can be inserted into the amniotic cavity of an embryo of these gestational ages. Customized catheters have been made to enable placement of the implanted tumor cells into the subcutaneous space while guarding against implantation into the underlying body cavities (i.e., cranium, thorax or abdomen) where tumor growth would threaten the life of the fetus.

Placement of the implanted tumor cells is partially dictated by the ability to manage the tumor growth in the period between birth and transplantation of the tumor to its anatomically appropriate site (e.g., brain for brain tumor cells).

The particular tumor cells used in the invention also are not critical. Any of a variety of human or other cancers can be studied using the animals of the invention as models. The use of cells derived from spontaneously occurring tumors as the starting material for implants ensures that genetic abnormalities that are found in spontaneously arising tumors are included in the model.

Examples of cancers that can be studied using the models of the invention include skin cancers (e.g., malignant melanoma), breast cancers, prostatic cancers, testicular cancers, ovarian cancers, adrenal cancers, cardiac tumors, lung neoplasms, urinary tract cancers, esophageal tumors, gastric tumors, intestinal tumors (colon cancer), laryngeal tumors, liver tumors, pancreatic cancers, and brain cancers.

Sources for appropriate cell cultures useful in the invention are well known to those skilled in the art. For instance, tumor cells isolated from a patient can be used as a source. Alternately, cultures of tumor cells from spontaneously derived human cancers have been established and are available from the American Type Culture Collection, Rockville, Md.

As noted, canines are particularly useful as models of brain cancer. Tumors in the central nervous system arise in the brain or spinal cord or may spread from other sites of cancer through the process of metastasis. Primary brain tumors arise from glial cells (astrocytoma, oligodendroglioma, ependymoma, glioblastoma) or supporting tissue (meningioma, schwannoma, papilloma of the choroid plexus). In addition, tumors arising from primitive cells (medulloblastoma, neuroblastoma, chordoma) can be used.

Preferably, the tumor cells or tumors are located in the animal's organ in which they normally occur. This preference can typically be achieved by initially introducing the tumor cells in the desired organ where such implants would not compromise fetal viability or the canine's survival until adulthood. Instances where such is the case are unknown. Alternately, subcutaneously implanted tumors can be removed surgically and transplanted to sites representative of the natural location of the tumors (i.e., brain for brain tumors, colon for colon tumors, ovary for ovarian tumors, and the like).

One of skill will recognize that there are a number of approaches to the use of animals of the invention for the design and screening of antineoplastic treatments. The animals could be used to conduct classical clinical trials on the efficacy of new cytotoxic drugs. Two identical groups of animals with tumors are treated with two different drugs; the outcome from treatment is measurable by change in tumor size over time. The animals whose tumors shrunk or failed to grow as fast would have received the more effective treatment. Response to classic therapies (e.g., the alkylating agent, BCNU, for brain tumors) could be applied as treatment to determine whether new drugs are better than current strategies (Phase II/III clinical trial).

Experimental oncologists (cancer treatment researchers) would exploit this model to improve the delivery of current cancer therapies. These therapies include implantable delivery pumps containing chemotherapeutic agents, engineered sponges that give a controlled release of drug, selective catheterization for local drug delivery, and other refinements in chemotherapy regimens. The ability to preserve bone marrow by genetically engineered growth factors while administering cytotoxic chemotherapy could be studied aggressively in this model.

One of skill would recognize an especially useful application of the animals of the invention would be to evaluate gene therapy (viral vector treatment). Viruses have been engineered to contain a gene-coding enzyme (tyrosine kinase) that makes virus-infected cells exquisitely sensitive to a certain agent (ganciclovir, an antiherpetic drug). Only cells infected with virus would be killed by the drug treatment. The long-term efficacy and safety of this paradigm of cancer treatment are unknown. Using such viral vectors to treat heterologous tumor in immunocompetent canines would be an expeditious method to determine the potential utility of this strategy. Because the canines have the ability to survive for months or years, long-term effects of treatment can be assessed.

Another application apparent to one of skill would be to isolate tumor cells from the tumor-bearing canines and use these cells to provoke an immune response in harvested lymphocytes from the canine in vitro. Such immune-based therapy can include genetic manipulation of the tumor cells to make the tumor more immunogenic (or foreign). Because the immune system of the canine is more human-like than that of a rodent, the results from such studies would be closely akin to an anticipated response in man.

Finally, but not lastly, the model is amenable to new surgical and radiological interventions against cancer. One of skill would appreciate that canines are sufficiently large to allow development of new surgical approaches to tumor resection. Furthermore, the animal is large enough to serve as a tool in the development of stereotactic or external beam radiation protocols.

The model is attractive from the perspective of a clinical follow-up because the diagnostic tools of computerized tomography (CT), magnetic resonance spectroscopy/imaging (MRS/MRI), and positron emission tomography (PET) could be used to monitor the tumor response. One of skill would recognize that this model uniquely affords controlled clinical evaluation for the further development of noninvasive radiological techniques to assess tumor response. This potential is infeasible in rodent systems or in randomly occurring canine tumors.

There are also basic tumor biology experiments that may be uniquely available because of this model. One of skill would exploit this model for a variety of experiments. These include studies of the biochemical processes involved in spontaneous tumor metastasis, the role of local immunosuppressive compounds released by tumor cells on tumor survival, and the influence of new blood vessel formation (angiogenesis) on tumor progression.

EXAMPLE

Pregnant beagles were gestationally staged by measuring amniotic sac diameters and fetal crown-rump lengths with ultrasound using standard techniques. When the pups reached the 36th gestational day, the dam was preanesthetized with valium and ketamine, then anesthetized using isofluorene (1.5%). A midline incision was made in the abdomen and each horn of the uterus retrieved in sequence. Fetal pups were imaged by intraoperative ultrasound to confirm their viability and to assess orientation in the uterine cavity. A 3-4 mm cutdown was made using monopolar cutting (15 watts) through the uterine wall of each chamber to a depth approximating the depth of the endometrium. This cutting minimizes bleeding and enables passage of instruments through the uterine wall.

A self-sealing, self-retaining plastic introducer (FIG. 1) was prepared to facilitate endoscopic access to the placental cavity while preserving amniotic fluid. The introducer was modified from a commercially available arterial introducer (Check-Flo™, Cook, Bloomington, Ind.). The top (entry portion) of introducer was unchanged. The lower exit portion of the introducer was fitted with a one piece machined plastic syringe barrel (1 ml) ground to have a shape allowing it to be "self-retaining" in the incision through the wall of the uterus. As shown in FIG. 1 the introducer 1 comprises a groove 3 and a holding rim 5 which together serve to retain the introducer 1 in the uterine muscle (delineated by the dashed lines). A foot plate 7 prevents inadvertent advancement of the introducer 1 into the incision. The introducer also comprises a self-sealing septum 9 and a flushing port 11. A pointed guide is used to insert the introducer 1 into the incision.

The introducer establishes a port of entry for a 3.7 mm (o.d.) endoscope 13 that includes a 30° lens 15 and a 1-mm (o.d.) working channel through which a 22 gauge flexible catheter 17 with a 30 gauge needle tip 19 is advanced. Fetuses were inspected visually to determine the site of cell implantation (typically the flank, just anterior to the hind leg). The 22 gauge flexible catheter 17 was passed through the endoscope 13 and advanced until visible in the field of the endoscope. The needle 19 was placed onto the fetal skin, then advanced further tangentially into the skin until the bevel of the needle was below the surface. Forty to 50 microliters of tumor cell suspension were deposited subcutaneously; the deposition was plainly visible through the endoscope. The needle was withdrawn, the endoscope retrieved, and the uterine wound closed in a cross-stitch fashion (4-0 chromic suture) after removing the introducer.

Each fetus was imaged and implanted in sequence until all the fetuses in the litter had been implanted. Nonviable fetuses (no heartbeat on ultrasound) were not implanted. The uterus was reinstalled into the abdomen and the incision closed in conventional fashion.

Fetal development (crown-rump length and head diameter) was followed by ultrasound imaging two to three times a week until normal vaginal delivery. The dam delivered in a temperature-controlled birthing kennel, lined on the bottom with (in sequence from bottom to top) electric heating blankets, towels, a wire mesh, and additional bedding (shredded newspaper). Puppies were examined for physical defects, and weighed daily or on alternate days.

Most recently, of eight fetuses implanted, six developed to term, one died after delivery, and five showed normal postnatal development. Three pups had palpable tumors in the subcutaneous space on the flank region. Tumors from fetal implants have appeared as late as 1 year after delivery.

When individual pups require identification relative to the implant procedure, a caesarean delivery is required because otherwise the pups are randomly delivered vaginally according to no known sequence.

Subcutaneous tumors from earlier litters have progressed to larger lesions. Routine hematoxylin and eosin (H&E) staining and immunohistochemical analysis for glial fibrillary acidic protein (GFAP) of biopsied specimens of the tumor confirmed the glial origin of the tumor. Cytogenetic analysis of short-term cultured cells from the biopsied tumor indicated that the tumor contained the same marker chromosomes as the cells used for the fetal implant. Chromosome analysis showed that the tumor cells were derived from the implanted cells.

The result validates the approach of using protracted subcutaneous exposure to allogeneic tumor cells in fetal canines to induce immune tolerance during the window of immune competency development. The tolerized animals are able to serve as hosts of tumor cells for subsequent studies of cancer biology, treatment, diagnosis and genetics.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of producing a canine useful for screening solid-tumor cancer therapies, the method comprising:

introducing heterologous tumor cells subcutaneously, into an immature preimmunocompetent canine fetus between about 35 and about 40 days gestation under conditions that induce specific immune tolerance to the tumor cells such that the canine, upon birth and thereafter, retains a normal, intact immune system and the tumor cells are recognized as self; and allowing the tumor cells to proliferate in the canine thereby forming a tumor.

2. The method of claim 1, wherein the fetus is between about 36 and about 38 days gestation and wherein said canine is a beagle.

3. The method of claim 1, wherein the tumor cell is allogeneic.

4. The method of claim 1, wherein the tumor cell is xenogeneic.

5. The method of claim 4, wherein the tumor cell is from a human tumor.

6. The method of claim 1, wherein the tumor cell is from a brain tumor.

7. The method of claim 1, wherein the tumor cells are introduced subcutaneously to allow for easy removal of the tumor for transplantation.

8. The method of claim 1, further comprising the step of transplanting tumor to a desired organ in said canine.

9. A method of producing a canine useful for screening solid-tumor cancer therapies, the method comprising:

introducing an antigen associated with tumor cells into an immature preimmunocompetent canine fetus between about 35 and about 40 days gestation under conditions that induce specific immune tolerance to the antigen such that the canine, upon birth and thereafter, retains a normal, intact immune system and such that tumor cells expressing said antigen are recognized as self;

introducing tumor cells expressing said antigen into the canine; and allowing the tumor cells to proliferate in the canine, thereby forming a tumor.

10. The method of claim 9, wherein the fetus is between about 36 and about 38 days gestation and wherein said canine is a beagle.

11. The method of claim 9, wherein the antigen is on the surface of a normal cell.

12. The method of claim 9, wherein the antigen is allogeneic.

13. The method of claim 9, wherein the antigen is xenogeneic.

14. The method of claim 13, wherein the tumor cell is from a human tumor.

15. The method of claim 9, wherein the tumor cell is from a brain tumor.

16. The method of claim 9, wherein the tumor cells are introduced subcutaneously to allow for easy removal of the tumor for transplantation.

17. The method of claim 9, further comprising the step of transplanting the tumor to a desired organ in the animal.

18. A canine comprising a heterologous solid tumor, wherein said canine is specifically immunotolerant of said tumor, such that the canine has a normal, intact immune system and the tumor cells are recognized as self.

19. The canine of claim 18, wherein the tumor is xenogeneic.

20. The canine of claim 19, wherein the tumor is a human tumor.

21. The canine of claim 18, wherein the tumor is a brain tumor.

* * * * *